(12) United States Patent
Jennings

(10) Patent No.: US 6,587,195 B1
(45) Date of Patent: Jul. 1, 2003

(54) METHOD AND APPARATUS FOR SEALING AN OPTICAL WINDOW IN A SPECTROSCOPIC MEASURING DEVICE

(75) Inventor: Norman A. Jennings, Los Alimitos, CA (US)

(73) Assignee: Axiom Analytical, Inc., Irvine, CA (US)

( * ) Notice: Subject to any disclaimer, the term of this patent is extended or adjusted under 35 U.S.C. 154(b) by 0 days.

(21) Appl. No.: 09/491,989

(22) Filed: Jan. 26, 2000

Related U.S. Application Data

(60) Provisional application No. 60/117,446, filed on Jan. 26, 1999.

(51) Int. Cl.[7] .................................................. G01N 1/10
(52) U.S. Cl. ...................................... 356/246; 250/343
(58) Field of Search ................................ 356/246, 440; 250/343, 428

(56) References Cited

U.S. PATENT DOCUMENTS

| | | | | |
|---|---|---|---|---|
| 4,580,901 A | * | 4/1986 | Goldsmith | 356/246 |
| 5,003,174 A | * | 3/1991 | Datwyler et al. | 250/343 |
| 5,223,716 A | * | 6/1993 | Rossiter | 250/343 |
| 5,905,271 A | * | 5/1999 | Wynn | 250/573 |
| 5,949,536 A | * | 9/1999 | Mark | 356/246 |

* cited by examiner

Primary Examiner—Frank G. Font
Assistant Examiner—Layla Lauchman
(74) Attorney, Agent, or Firm—Myers Dawes Andras & Sherman LLP; Joseph C. Andras

(57) ABSTRACT

The invention comprises a spectroscopic measuring device, a seal for such a device, and a method for sealing such a device. A window having a first and second portion is disposed in a cavity of a housing. The first portion is adjacent to an exterior of the device and has a first diameter less than a second diameter of the second portion, thus forming a shoulder therebetween and defining a gap between the first portion and an interior housing surface. An intermediate ring with a, metallic coating is disposed in the gap adjacent to the shoulder. A retaining ring is disposed in the gap adjacent to the intermediate ring. An exposed surface of the retaining ring is flush with an end housing surface and an exposed sapphire surface. A portion of the exposed retaining ring surface is electron beam welded to a portion of the end housing surface. The housing, intermediate ring, and retaining ring comprise a nickel-molybdenum-chromium alloy. A method for sealing a spectroscopic device is disclosed as comprising the steps of: disposing a window with a shoulder in a cavity of a housing; disposing an intermediate coated O-ring or C-ring adjacent to the shoulder and between the window and the housing; disposing a retaining ring adjacent to an exterior of the device and between the window and the housing; electron-beam welding a portion of an exposed retaining ring surface to a portion of an end housing surface.

7 Claims, 10 Drawing Sheets

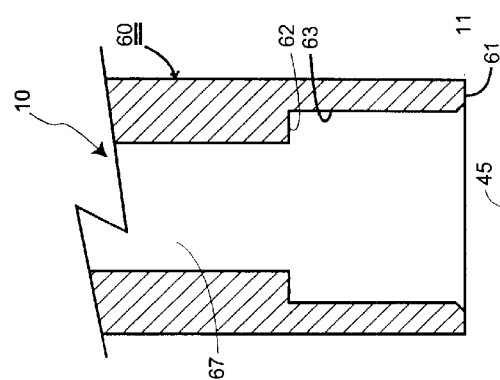
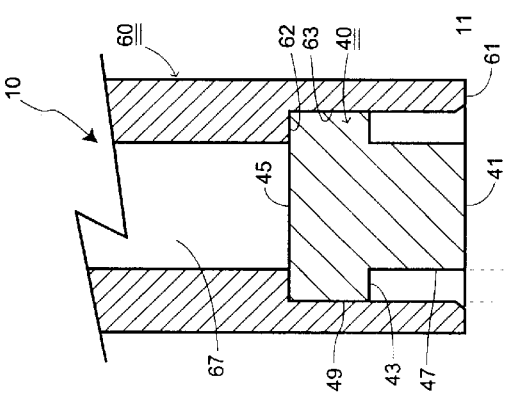
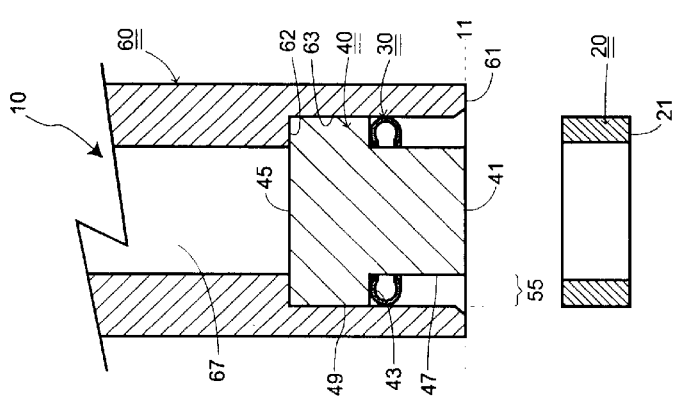
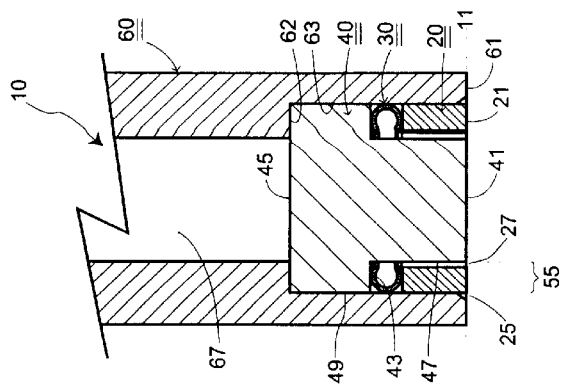
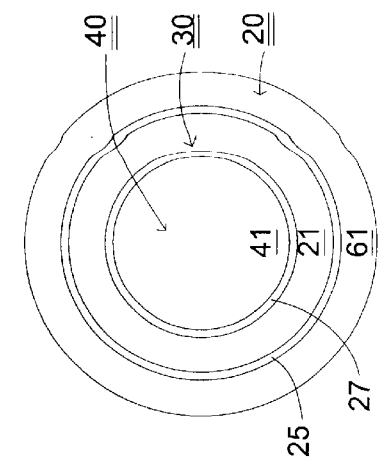

METHOD AND APPARATUS FOR SEALING AN OPTICAL WINDOW IN A SPECTROSCOPIC MEASURING DEVICE

This application claims the benefit of Provisional application No. 60/117,446, filed Jan. 26, 1999.

BACKGROUND OF THE INVENTION

1. Field of the Invention

The invention relates generally to seals for spectroscopic measuring devices and, more particularly, to a method and apparatus for sealing an optical window in a spectroscopic measuring device.

2. Description of Prior Art

In the chemical process industry, spectroscopic measuring devices are often used to analyze reactions. Such devices are often provided as specialized probes or as flow cells of minute proportions. They typically use ultraviolet to visible ("UV-VIS") or infrared ("IR") radiation. As such, these devices typically include an optical element that separates the measuring device's optical paths from the reaction while transmitting the necessary radiation. The optical elements, therefore, must have great mechanical strength, high resistance to chemical attack, and broad optical transmission range. A sapphire window is commonly used as the optical element commonly in such devices, but other materials may be sued where desired.

It is important, of course, to seal the optical element to its surrounding structure. The prior art consists of various methods of sealing the typically non-metal optical element to the typically metallic housing of the measuring device.

However, the prior art has inadequately dealt with the various environmental problems encountered in chemical processes that may cause the seal to fail, thereby rendering the measuring device inoperable and possibly harming nearby operators. These environmental problems include low temperatures, high temperatures, extreme temperature cycling, high pressure, fluctuations in pressure, and aggressive chemical reaction. Not only do chemical processes range in temperature from cryogenic to 500 degrees Celsius ("C") or more, the rate of change in temperature may be up to 50 C. per minute. Such temperature cycling causes materials to expand and contract and may cause a conventional seal to leak. Temperature cycling is especially troublesome with materials having a high thermal coefficient of expansion and at junctions between materials having different coefficients of expansion. Changes in pressure can also affect the expansion of materials. Harsh chemical reactions attack and wear away the composition of a material. In addition, spectroscopic measuring devices, such as probes and flow cells, tend to be relatively small in size, thereby reducing the range and flexibility of dimensions and materials available in making a seal.

The prior art has attempted to address these environmental problems by using elastomeric seals, by brazing sapphire to metal, and by "sweating" the window directly to the metal housing. Each of these prior art methods and structures has its disadvantages when encountering either temperature cycling or aggressive chemical reaction.

A poplular elastomeric seal, for example, is a high performance perfluoroelastomer O-ring. Though highly chemically resistant, such O-rings may expand up to 20% at upper temperatures near 280–300 C. As such, frequent and broad temperature cycles may cause these elastomeric seals to leak. Moreover, repeated temperature cycling may cause them to harden. The same problems are encountered with filled polymer, usually Teflon based, metal spring energized seals.

Brazing consists of bonding sapphire to a metallic housing by metalizing the perimeter sealing surface of the sapphire with specialized materials and then brazing that surface to a metal housing. Since sapphire has a low thermal coefficient of expansion, it is likewise preferable to use a specialized material with a low thermal coefficient of expansion in order to provide a more reliable seal that is less likely to leak. However, a dilemma exists in that most low expansion metals have high iron content, thus making them susceptible to attack by chemical processes. A more chemically resistant metal, however, usually has a higher thermal coefficient of expansion.

Sweating consists of fitting the window directly in the metal housing without use of additional materials. However, the differing thermal coefficients of expansion between the sapphire and the parent metal, such as nickel alloy, may cause leaks to occur at or above 280 C.

There remains a need, therefore, for a spectroscopic measuring device having an improved seal structure.

BRIEF SUMMARY OF THE INVENTION

In accordance with the present invention, both a structure and method are disclosed which overcome these obstacles. Structurally, the invention comprises both a spectroscopic measuring device as well as a seal for a spectroscopic measuring device.

The invention comprises a housing, a window, an intermediate ring, and a retaining ring. The housing comprises a first material and defines a cavity. The first material is preferably a metallic alloy such as nickel-molybdenum-chromium alloy. Disposed in the cavity, the window has a first portion adjacent to an exterior of the device and a second portion. The first portion has a first diameter and a first side wall. The second portion has a second diameter and a second side wall. The second diameter is larger than the first diameter such that a shoulder is formed between the second and first portion and a gap is defined between the first side wall and an interior surface of the housing.

The intermediate ring is disposed in the gap adjacent to the shoulder of the window. The intermediate ring comprises an annular C-ring or an O-ring and has a coating of material with a higher thermal coefficient of expansion than that of the ring itself. Such a coating may comprise gold plating, or silver, or platinum.

The retaining ring is disposed in the gap adjacent to the intermediate ring. The retaining ring has an exposed retaining surface that is flush with both an end housing surface of the housing and an exposed sapphire surface of the window. An outer juxtaposition is defined between the retaining ring and the housing while an inner juxtaposition is defined between the retaining ring and the window. A portion of the exposed retaining surface is electron beam welded to a portion of the end housing surface at the outer juxtaposition.

The retaining ring and the intermediate ring comprise the first material of the housing.

In an alternate embodiment, the exposed sapphire surface of the window is not flush with the exposed retaining surface of the retaining ring. Thus, only an outer juxtaposition is defined between the retaining ring and the housing. A portion of the exposed retaining surface is electron beam welded to a portion of the end housing surface at the outer juxtaposition.

In an alternate embodiment, a gasket is provided and displaced between the shoulder of the housing and the inner surface of the window.

The invention further comprises a method for sealing a spectroscopic measuring device 10. The method comprises the steps of: disposing a window 40 in a cavity 65 of a housing 60; disposing an intermediate ring, which may comprise a metallic C-ring 30 or O-ring 30a for example, in the cavity 65 adjacent to the window 40; disposing a retaining ring 20 in the cavity adjacent to an exterior of the device 10 and the intermediate ring 30 or 30a; and welding a portion of an exposed retaining surface 21 of the retaining ring 20 to a portion of an end housing surface 61 of the housing 60.

The preferred method involves pressing the retaining ring 20 into the cavity so as to crush the intermediate ring 30, 30a as appropriate. Preferably, until contact is made during an initial part of the press-fitting of the retaining ring 20, a thin tube is inserted between the outside diameter of the window's first portion 42 and the inside diameter of the retaining ring 20 in order to center the intermediate ring 30, 30a and thereby provide a more reliable seal.

The method may further comprise the step of coating the intermediate ring 30 with a plating material having a higher thermal coefficient of expansion than a thermal coefficient of expansion of the intermediate ring, such as gold. The method also comprises the step of providing a shoulder 43 on the window 40, wherein the step of disposing the intermediate ring 30 or 30a in the cavity adjacent to the window 40 comprises the step of disposing the intermediate ring 30 or 30a adjacent to the shoulder 43 of the window 40.

The step of welding the portion of the exposed retaining surface 21 of the retaining ring 20 to the portion of the end housing surface 61 of the housing 60 preferably comprises the step of electron beam welding the portion of the exposed retaining surface 21 to the portion of the end housing surface 61. Other methods of sealing the two surfaces, however, may be used with equal applicability.

The step of disposing the retaining ring 20 in the cavity 65 adjacent to the exterior of the device 10 and the intermediate ring 30 may comprise the step of disposing the retaining ring 20 such that an exposed retaining surface 21 of the retaining ring 20 is substantially flush with an exposed sapphire surface 41 of the window 40 and the end housing surface 61 of the housing. The window 40, however, may be recessed or even extend in other embodiments.

The invention, now having been briefly summarized, may be better visualized by turning to the following drawings wherein like elements are referenced by like numerals.

BRIEF DESCRIPTION OF THE DRAWINGS

FIGS. 2a to 2d are sectional side views of the present measuring device 10 in various states of assembly;

FIG. 3 is an end plan view of the first preferred embodiment;

The invention and its various embodiments can now be better understood by turning to the following detailed description wherein the illustrated embodiments are described. It is to be expressly understood that the illustrated embodiments are set forth as an example and not by way of a limitation to the invention as ultimately defined in the claims.

DETAILED DESCRIPTION OF THE PREFERRED EMBODIMENTS

The invention comprises a spectroscopic measuring device, a seal for such a device, and a method for sealing such a device. A window having a first and second portion is disposed in a cavity of a housing. The first portion is adjacent to an exterior of the device and has a first diameter less than a second diameter of the second portion, thus forming a shoulder therebetween and defining a gap between the first portion and an interior housing surface. An intermediate ring with a metallic coating is disposed in the gap adjacent to the shoulder. A retaining ring is disposed in the gap adjacent to the intermediate ring. An exposed surface of the retaining ring is flush with an end housing surface and an exposed sapphire surface. A portion of the exposed retaining ring surface is electron beam welded to a portion of the end housing surface. The housing, intermediate ring, and retaining ring comprise a nickel-molybdenum-chromium alloy. A method for sealing a spectroscopic device is disclosed as comprising the steps of: disposing a window with a shoulder in a cavity of a housing; disposing an intermediate coated O-ring or C-ring adjacent to the shoulder and between the window and the housing; disposing a retaining ring adjacent to an exterior of the device and between the window and the housing; electron-beam welding a portion of an exposed retaining ring surface to a portion of an end housing surface.

Figure 1:
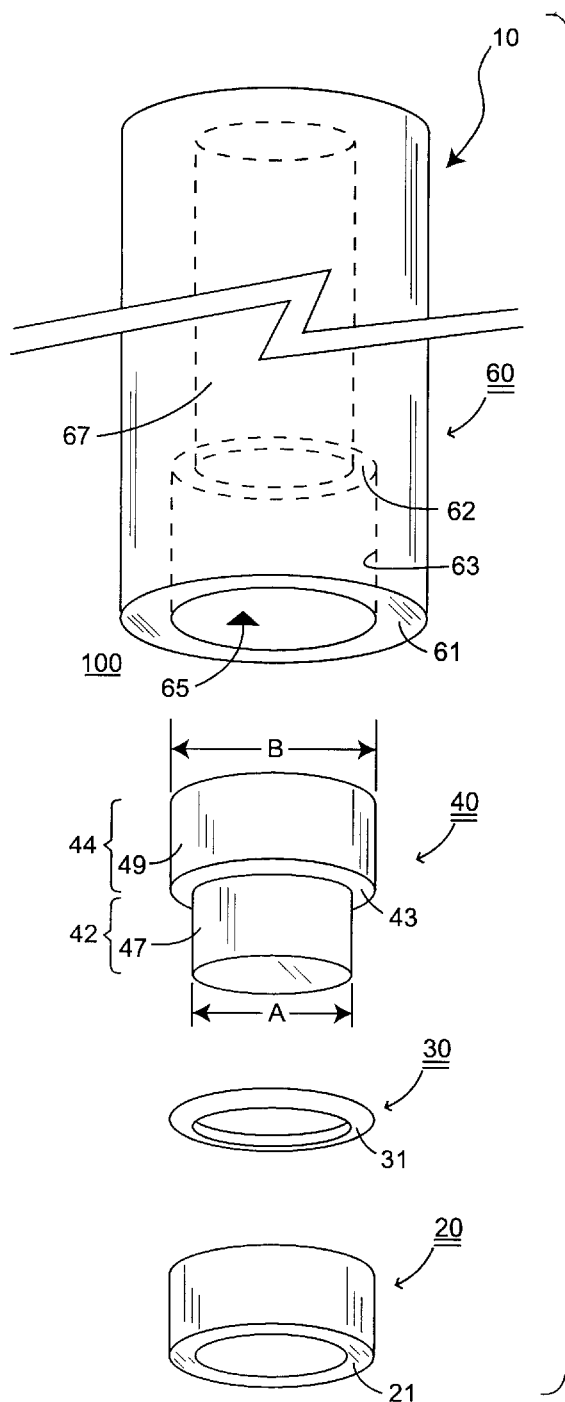
FIG. 1 is an exploded perspective view of a first preferred embodiment of the invention.

FIG. 1 is an exploded perspective view of a first preferred measuring device 10 according to this invention. The spectroscopic measuring device 10 is illustrated as a probe, but it may have other structural forms such as a flow cell. As shown, the preferred measuring device 10 generally comprises a housing 60, a window 40 (made e.g. of sapphire), an intermediate ring 30, and a retaining ring 20. The window 40, the intermediate ring 30, and the retaining ring 20, may be separately regarded as a seal for a spectroscopic measuring device.

The housing 60 has a cavity 65 adjacent to a pathway 67 and open to the exterior 100 of the measuring device 10. The housing 60 has an inner surface 63 and an annular shoulder 62. The housing 60 may comprise a metallic material or alloy, such as nickel alloy. In the preferred embodiment, the housing 60 comprises Hastelloy C276 alloy, which is a nickel-molybdenum-chromium alloy.

The window 40 has a first portion 42, a second portion 44, and a shoulder portion 43 therebetween. The first portion 42 has a first side wall 47 and a first diameter "A". The second portion 44 has a second side wall 49 and a second diameter "B" that is greater than the first diameter "A".

Figure 1A:
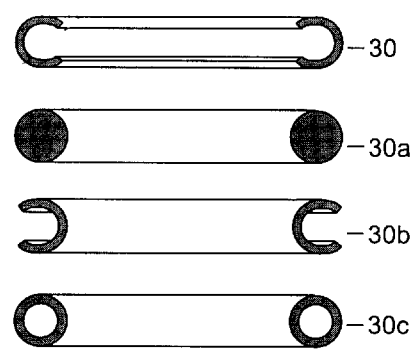
FIG. 1a are sectional views of several different seals that may be used in various embodiments of the invention.

An intermediate ring 30 is purchased as off-the-shelf item and then provided with a coating 31. The coating 31 may be any material with a thermal coefficient of expansion higher than that of the intermediate ring 30 itself. In the preferred embodiment, the intermediate ring 30 comprises a C-ring with gold plating. As shown in FIG. 1a, however, many forms of rings may be used including, for example, an inwardly-facing C-ring 30, a solid O-ring 30a, an outwardly-facing O-ring 30b, and a hollow O-ring 30c. If coated, moreover, many different materials may be used such as, for example, gold, platinum or silver.

The retaining ring 20 has an annular shape with an exposed surface 21. The retaining 20, intermediate ring 30, and housing 60 may all comprise the same material, such material being a nickel-molybdenum-chromium alloy in the preferred embodiment.

Figure 1B:
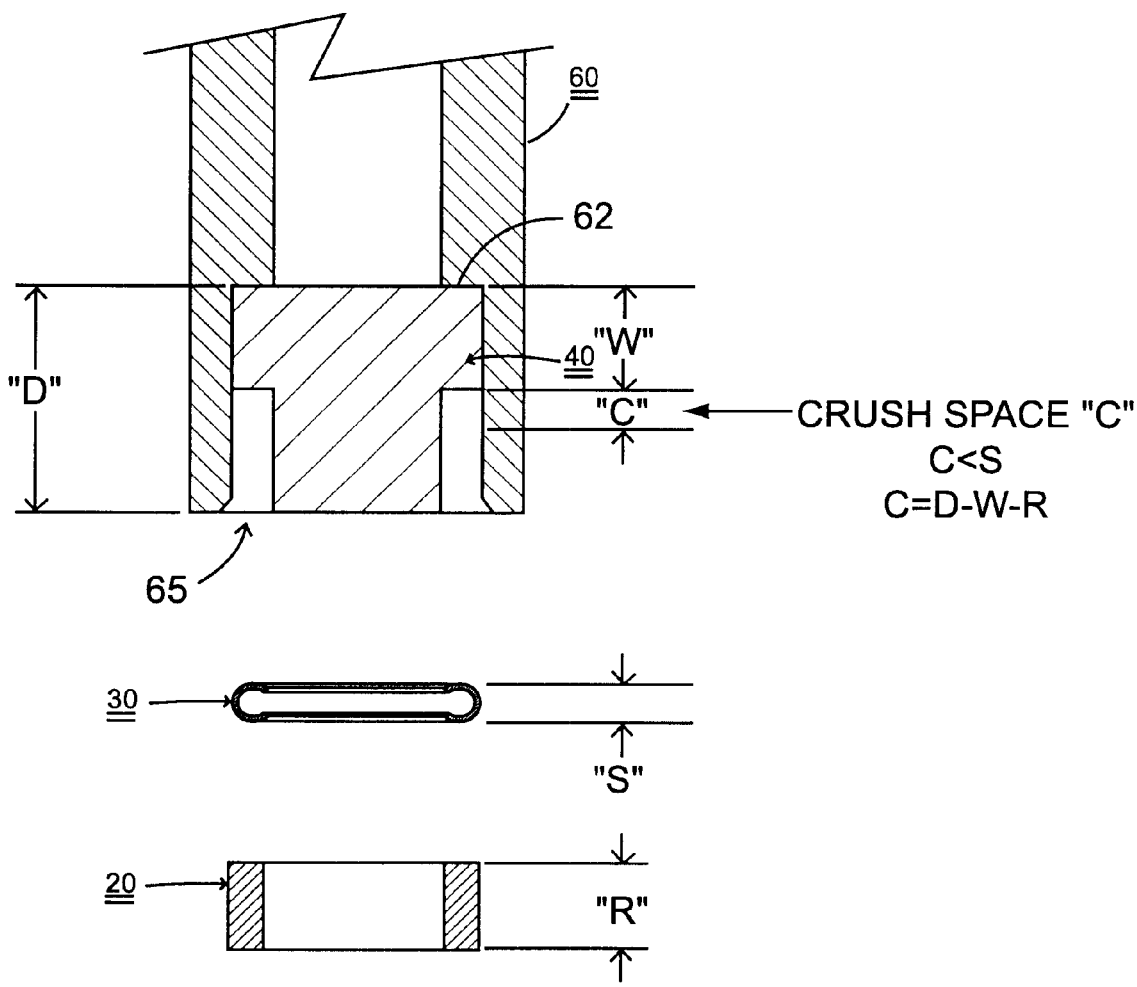
FIG. 1b is a sectional side view of the first preferred spectroscopic device showing the dimensions that are controlled to obtain a desired crush space "C" that is dimensionally appropriate for creating a reliable seal with an intermediate ring of thickness "S"

FIG. 1b is a sectional side view of a first preferred spectroscopic device 10, in a partial stage of assembly, with various dimensional features called out. In particular, the cavity or counterbore 65 has a depth "D", the window 40 has a thickness "W", the intermediate ring or seal 20 has a thickness "S", and the retaining ring 20 has a thickness "R". As suggested by the Figure, the intermediate ring 30 of thickness "S" will ultimately occupy a crush space of thickness "C" where C<S. The intermediate ring 30, in other words, will be compressed or energized such that it acts as a spring and presses back against the adjacent surfaces to form a reliable seal. To the inventor's best knowledge, energized seals have not been effectively used to seal a window to a metallic housing because of the difficulty in implementing a precise crush which is critical to the seal. Here, however, a precise crush space "C" may be defined by measuring counterbore depth "D", window annulus thickness "W" and ring thickness "S" (after coating if applicable), and then selecting or manufacturing a retaining ring of appropriate thickness "R" that provides the appropriate crush. In the preferred embodiment, the C-ring 30 is to be crushed by 0.010"+0.002". The retaining ring 20 need only be appropriate sized to achieve such compression based on the actual measurements of counterbore depth D, thickness W and thickness S. At present, the depth of the counterbore "D" is fairly consistent, but the C-rings 30 tend to have a relatively wide range of thickness "S" after being gold-plated. The thickness "W" of the window's annulus is also subject to some degree of variance. In this and in other embodiments of Applicant's inventions, however, these manufacturing tolerances may be accounted for by careful measurement and selection of the retaining ring's thickness "R."

The preferred embodiment varies the thickness "R" of the retaining ring 20. It is possible, of course, to take other measurements as they come and vary one or more other measurements to achieve the same affect.

FIGS. 2a to 2d are sectional side views of the present measuring device 10 in various states of assembly. The inner surface 45 of the window 40 is seated on the shoulder 62 of the housing 60. Thus, the inner surface 45 forms an interface between the window 40 and the pathway 67. The second portion 44 of the window 40 is sized such that its second wall 49 fit snugly against the inner surface 63 of the housing 60. Consequently, since the first portion 42 is of smaller diameter, a gap 55 is defined between the first wall 47 of the window 40 and the inner surface 63 of the housing 60. The intermediate ring 30, shown in FIG. 2 as a C-ring, is disposed in the gap 55 on top of, or adjacent to, the intermediate ring 30 between the first side wall 47 of the window 40 and the inner surface 63 of the housing 60. The retaining ring 20 is disposed (preferably press-fit) in the gap 55 on top of, or adjacent to, the intermediate ring 30. In the preferred embodiment, an exposed retaining ring surface 21 of the retaining ring 20 is flush with an end housing surface 61 and the exposed sapphire surface 41 of the window 40. Thus,, the measuring device 10 has an end device surface 11 defined by the end housing end surface 61, exposed retaining ring surface 21, and the exposed sapphire surface 41. In the preferred embodiment, the end device surface 11 is evenly flat throughout.

FIG. 3 is an end plan view of the present measuring device 10. In FIGS. 2 and 3, the retaining ring 20 is fitted such that a first, or outer, juxtaposition or seam 25 is defined between the housing 60 and the retaining ring 20, and a second, or inner, juxtaposition or seam 27 is defined between the retaining ring 20 and the window 40. The inner seam 27 may be closely juxtaposed to the first portion 42 of the window 40, or widely spaced (as shown), since the present embodiment assumes that system pressure will be applied via the seam 27.

At the outer seam 25, a portion of the retaining ring's exposed surface 21 is electron beam welded to a portion of the housing's end housing surface 61 to provide tightly formed seal. In the embodiment shown, a beveled anulus 63 is provided for containing a weld 28 (see FIG. 5), but other methods of sealing the outer seam 25 may be used.

Figure 4:
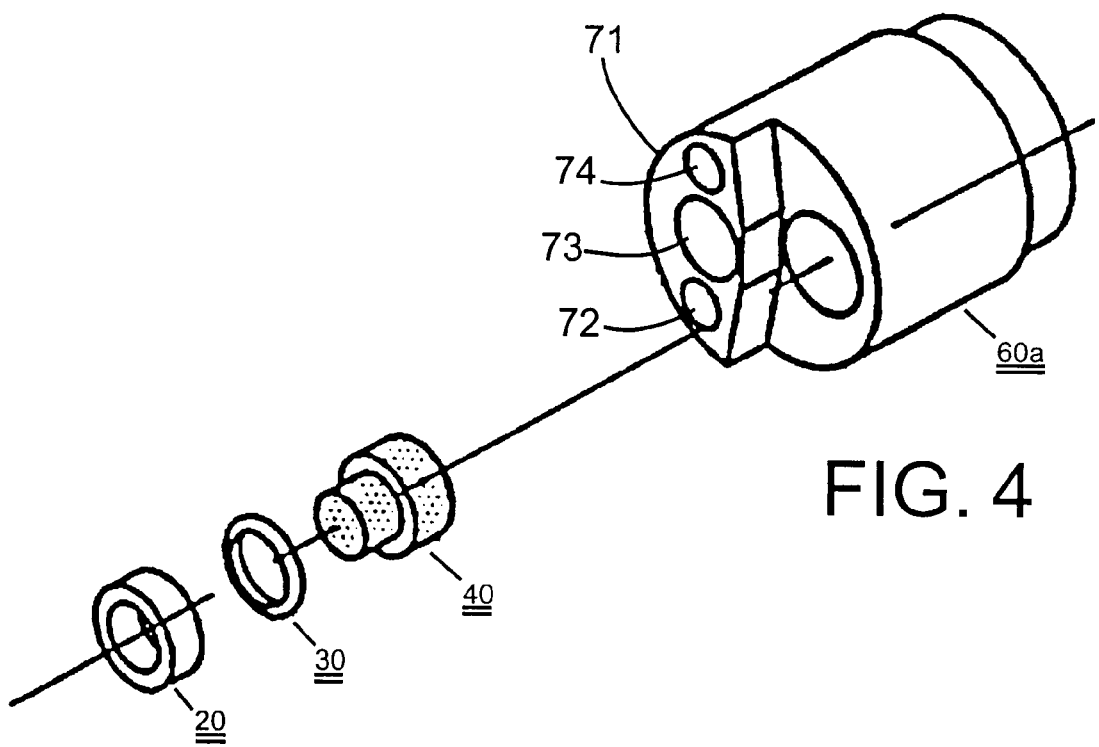
FIG. 4 is an exploded perspective view of the first preferred embodiment wherein the housing is provided in a top sensing head having multiple apertures.

FIG. 4 shows a "top sensing head" 60a as an alternate structure of the housing 60 discussed above, The sensing head 60a includes a raised surface 71 with multiple apertures 72, 73, 74 defined therein. The top sensing head 60a is used in certain ones of the assignee's spectroscopic immersion probes.

Having now described the base structure of the preferred embodiment, we turn now to its operation.

Figure 5:
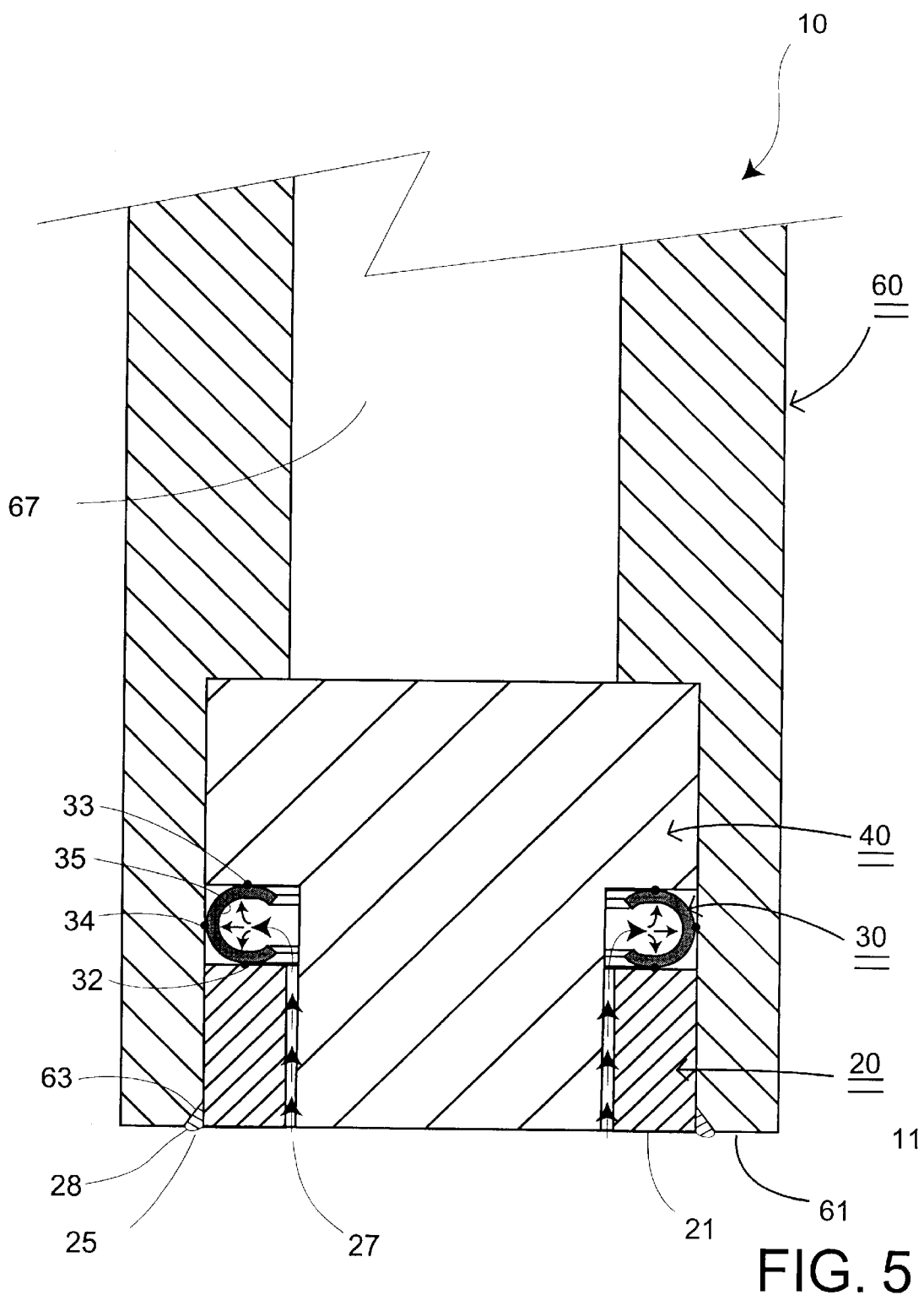
FIG. 5 is a sectional side view of the first preferred embodiment in operation.

FIG. 5 is a sectional side view of the present invention in operation. The spectroscopic device 10 may be subject to high pressure and to corrosive substances. As suggested by the arrows, the pressurized substances will attempt to enter the spectroscopic device 10 through the seal, i.e. by passing beyond the inner ring 30 via the outer seam 25 and the inner seam 27. However, in accordance with this embodiment, the inner seam 27 is the only practical way that the system pressure may enter the device 10, if at all, because the outer seam 25 is electron beam welded to the housing 61. The inner seam 27, moreover, may be tightly fitted so that any substance entering through it would be minimal (See FIG. 10 discussed below).

Assuming a small amount of substance actually enters through the inner seam 27, the substance will encounter the inner surface 35 of the C-ring 30 and, as shown by the arrows in FIG. 5, the substance will cause the C-ring 30 to expand outwardly to form an even tighter fit of the C-ring 30 against the surfaces of its neighboring components. More specifically, the contact points 32, 33, 34 between the C-ring 30, on the one hand, and the retaining ring 20, window 40, and housing 60, on the other hand, are reinforced by the expansion of the C-ring 30 caused by the pressure of the incoming substance. The gold plating 31 serves to thicken the C-ring 30, thereby also reinforcing the contact points 32, 33, 34. Gold is desirable because it is so malleable that it tends to fill in any micro-defects that may be present and thereby improve the seal. Moreover, since gold has a higher thermal coefficient of expansion than that of a nickel-molybdenum-chromium alloy as well as many other metallic alloys, the gold coating 31 will expand more rapidly, further increasing pressure along the contact points 32, 33, 34 and preventing any substance from entering through.

Figure 6:
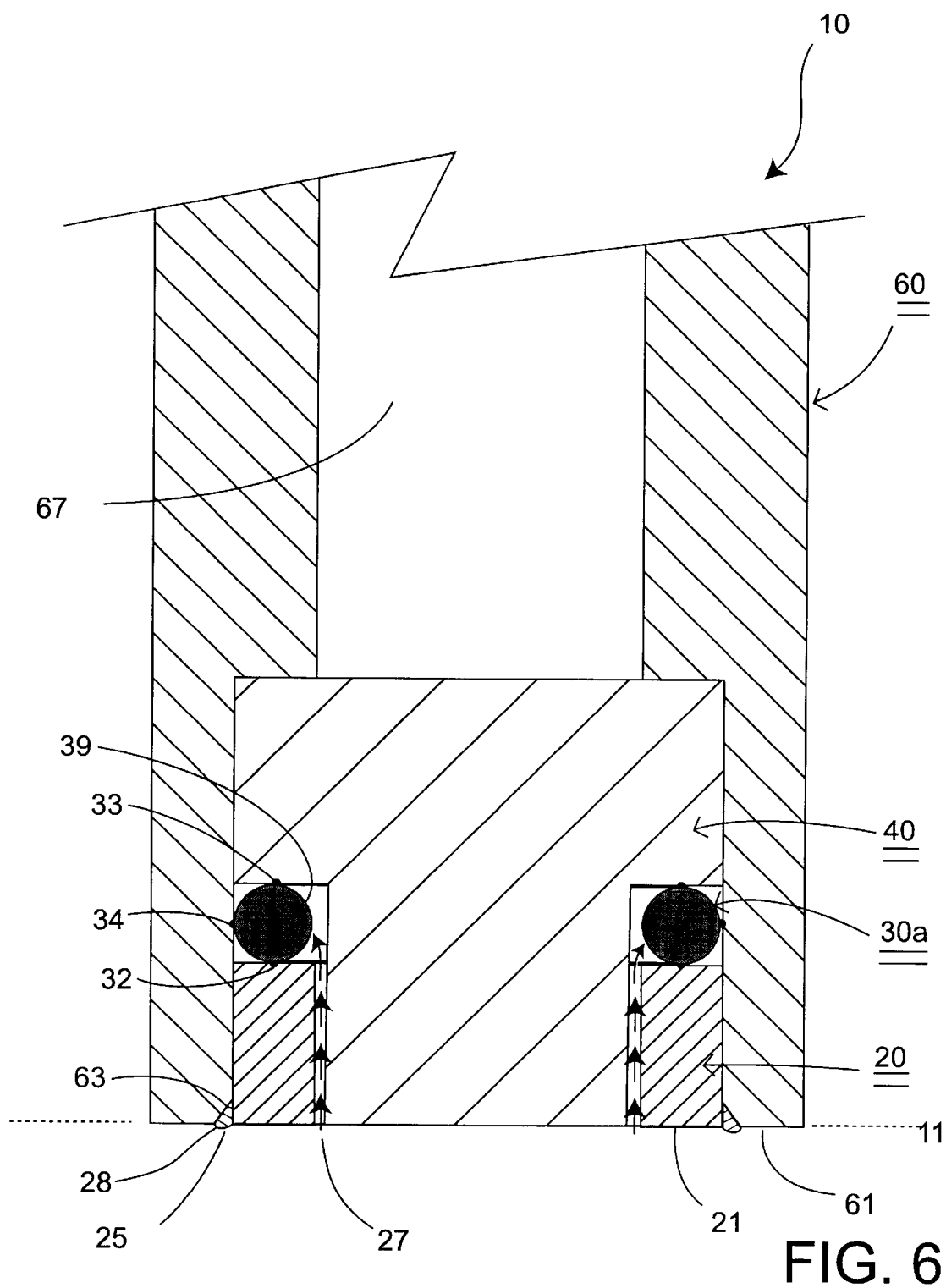
FIG. 6 is a sectional side view of an alternative embodiment of the invention that uses an intermediate O-ring rather than a C-ring.

FIG. 6 is a sectional side view of an alternative embodiment in operation, with the only difference from FIG. 5 being that the intermediate ring 30a is a solid metallic O-ring instead of a C-ring. Unlike the first embodiment, however, this embodiment does not reinforce the contact points 32, 33, 34, as with the first embodiment.

Figure 7:
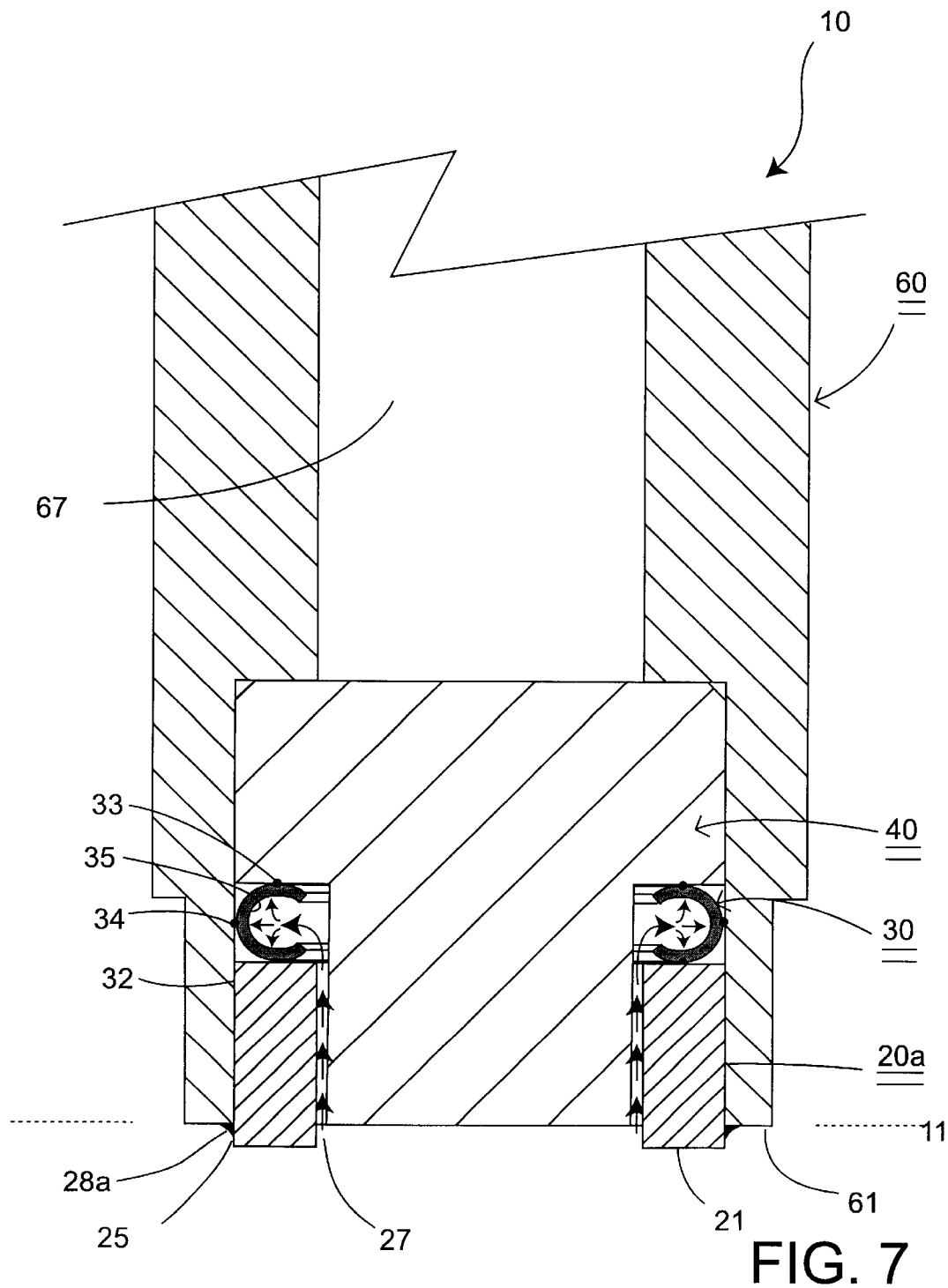
FIG. 7 is a sectional side view of an alternative embodiment of the invention that uses a taller retaining ring.

FIG. 7 is a sectional side view of an alternative embodiment in operation, with the only difference being that the retaining ring 20a is taller than the retaining ring 20 of FIG. 5. Here, therefore, the retaining ring 20a extends beyond the end surface 61 of the housing 50 and an external weld 28a is used.

Figure 8:
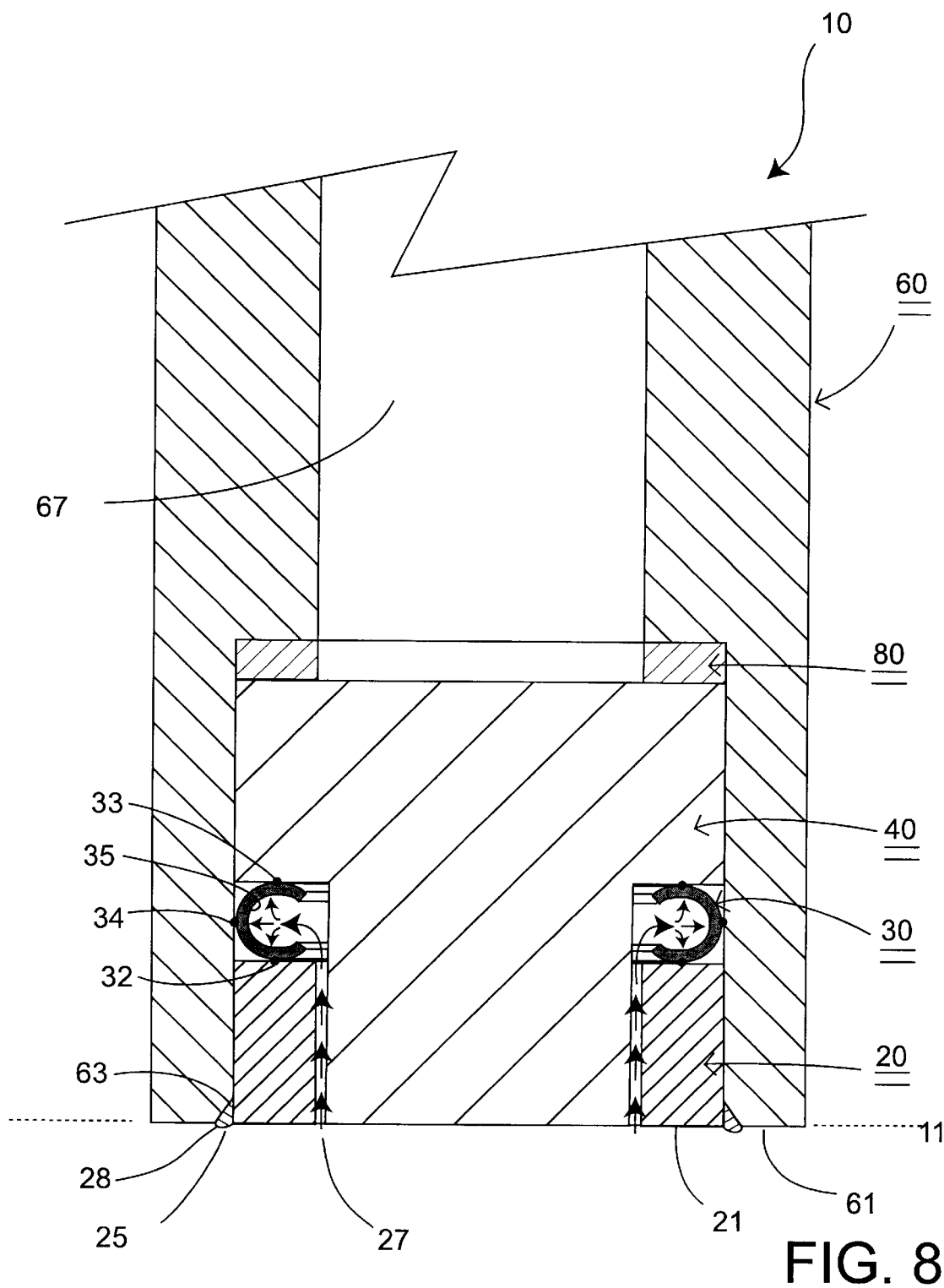
FIG. 8 is a sectional side view of an alternative embodiment of the invention that uses an expansion gasket.

FIG. 8 shows another alternate embodiment where the measuring device 10 further comprises a thermal-expansion gasket 80 disposed between the shoulder 62 of the housing 60 and the inner surface 45 of the window 40.

Figure 9:
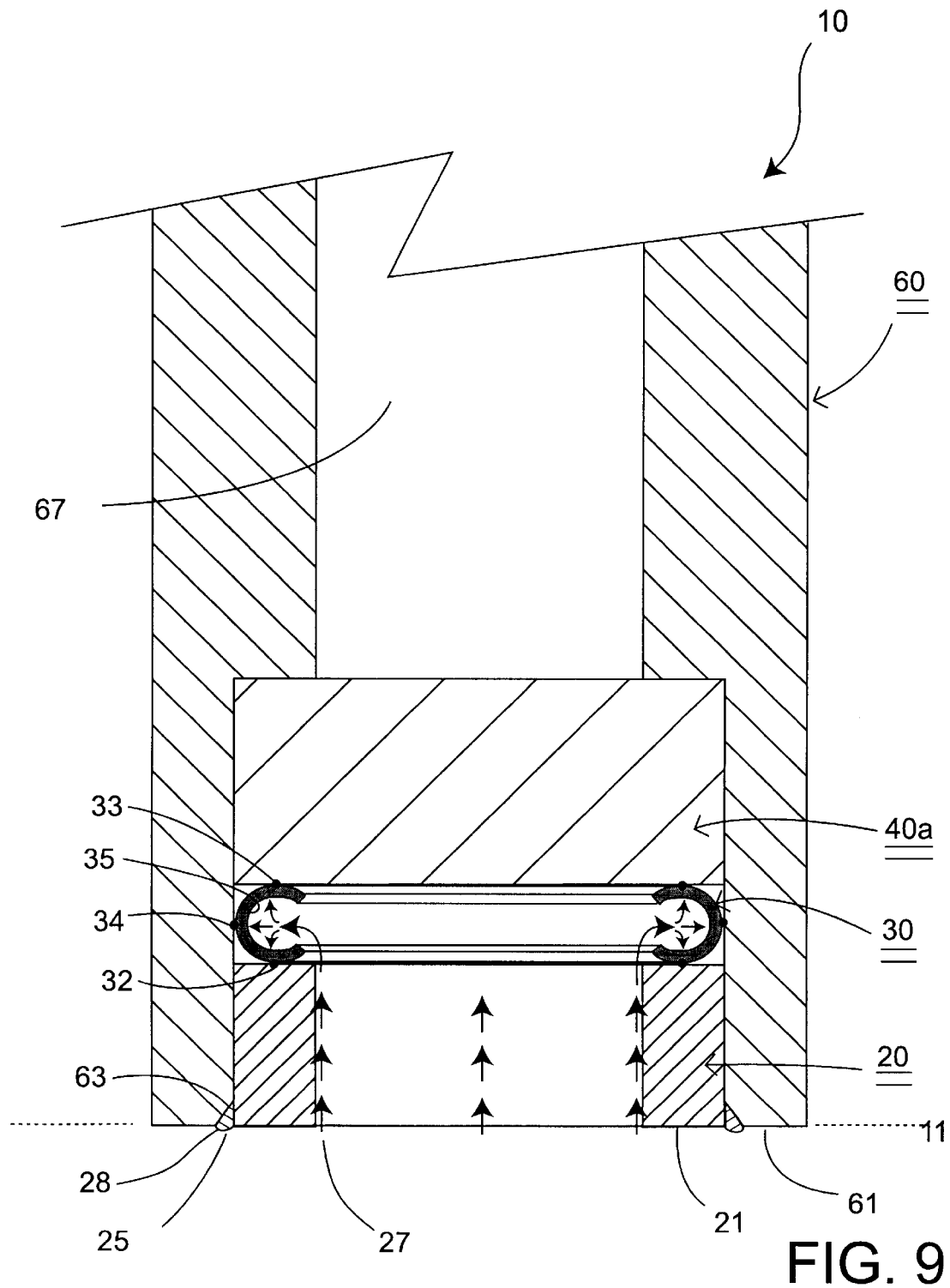
FIG. 9 is a sectional side view of an alternative embodiment of the invention that uses a disk-shaped window.

FIG. 9 is a sectional side view of yet another embodiment. Here, a window 40a is provided as a simple disk. As such, its top surface 41a is not flush with, but rather is substantially below, the exposed surface 21 of the retaining ring 20. The intermediate ring 30 is disposed in the cavity 65 and adjacent to the window 40. Though a C-ring 30 is shown in FIG. 9, this embodiment may also comprise an O-ring as the intermediate ring. The retaining ring 20 is disposed in the cavity 65 and adjacent to the intermediate ring 30.

Though a different window 41a is provided in FIG. 9, the same principles of operation apply. Specifically, any incoming substance will encounter the intermediate ring 30, causing it to expand and reinforce the contact points 32, 33, 34. Any incoming matter is prevented from entering past the contact points 32, 33, 34. Thus, the window may come in a variety of shapes.

Figure 10:
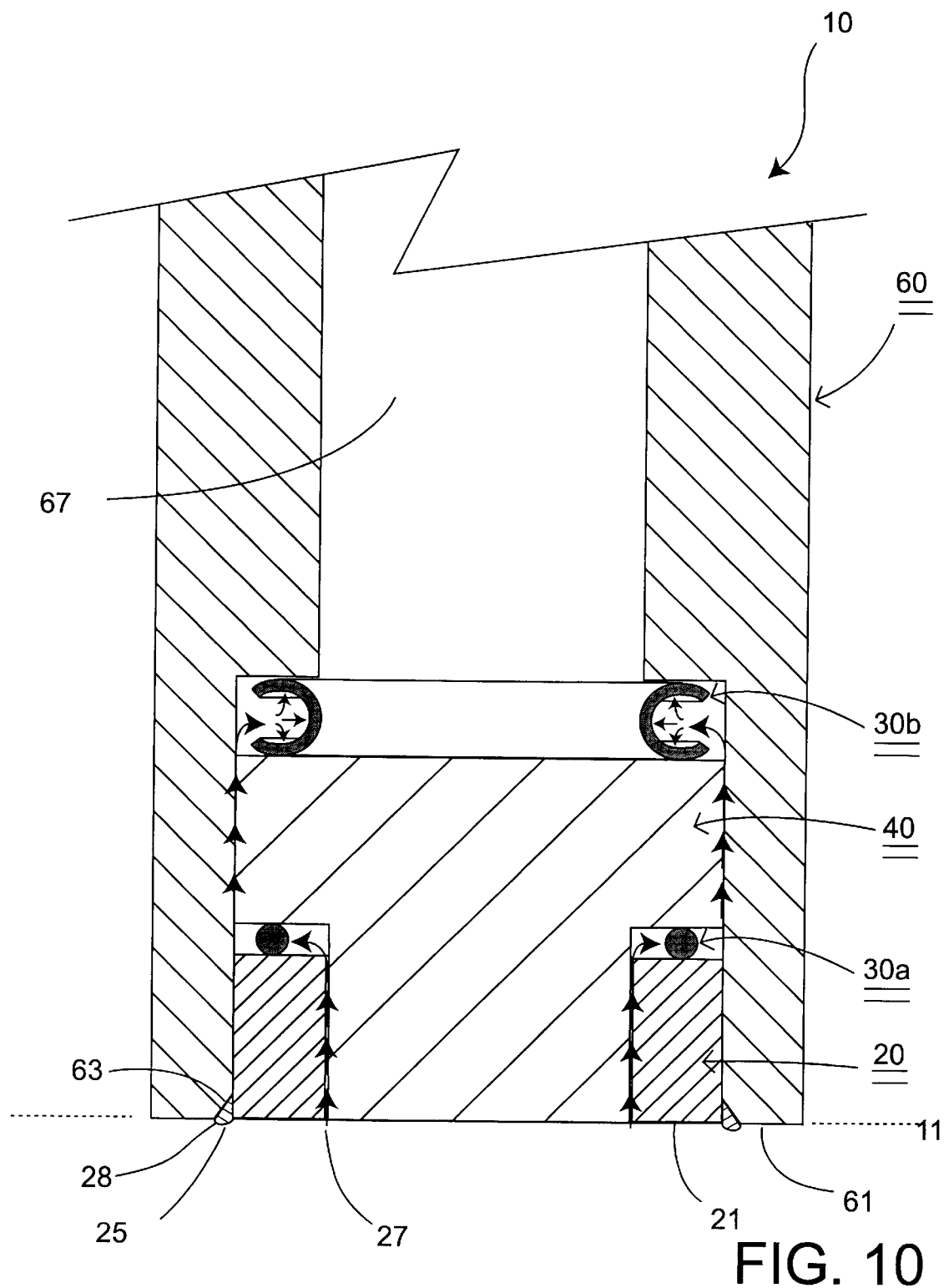
FIG. 10 is a sectional side view of an alternative embodiment of the invention that uses two intermediate rings.

FIG. 10 is a sectional side view of yet another embodiment. Here, the seal is doubly-formed by a first solid O-ring 30a (crushed between the annulus of the window 40 and the retaining ring 20) and by a second outwardly-opening C-ring 30b crushed between an upper surface of the window 40 and the shoulder of the cavity or counterbore 65. In this embodiment, the C-ring 30b may be centered by inserting an alignment rod or spindle from above (not shown), via the housing 60. Moreover, as suggested by the arrows, any system pressure that gets beyond the first seal 30a serves to reinforce the second seal 30b. It is possible, or course, to use any combination of like or dissimilar seals, such as those shown in FIG. 1a. Two C-rings may be used, for example, one inwardly-facing C-ring 30, and one outwardly-facing C-ring 30b such that both seals are reinforced by system pressure.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. The claims are thus to be understood to include what is specifically illustrated and described above, what is conceptionally equivalent, what can be obviously substituted and also what essentially incorporates the essential idea of the invention.

I claim:

1. A method for sealing a spectroscopic measuring device, the method comprising the steps of:

disposing a window in a cavity of a housing;

disposing an intermediate ring in the cavity and adjacent to the window;

disposing a retaining ring in the cavity and adjacent to an exterior of the device and the intermediate ring; and welding a portion of an exposed retaining surface of the retaining ring to a portion of an end housing surface of the housing.

2. The method in claim 1 further comprising the step of coating the intermediate ring with a plating material having a higher thermal coefficient of expansion than a thermal coefficient of expansion of the intermediate ring.

3. The method in claim 1 further comprising the step of providing a shoulder on the window, wherein the step of disposing the intermediate ring in the cavity and adjacent to the window comprises the step of disposing the intermediate ring adjacent to the shoulder of the window.

4. The method in claim 1 wherein the step of disposing the intermediate ring in the cavity and adjacent to the window comprises the step of disposing an O-ring in the cavity and adjacent to the window.

5. The method in claim 1 wherein the step of disposing the intermediate ring in the cavity and adjacent to the window comprises the step of disposing a C-ring in the cavity and adjacent to the window.

6. The method in claim 1 wherein the step of welding the portion of the exposed retaining surface of the retaining ring to the portion of the end housing surface of the housing comprises the step of electron beam welding the portion of the exposed retaining surface to the portion of the end housing surface.

7. The method in claim 1 wherein the step of disposing the retaining ring in the cavity and adjacent to the exterior of the device and the intermediate ring comprises the step of disposing the retaining ring such that the exposed retaining surface of the retaining ring is flush with an exposed sapphire surface of the window and the end housing surface.

* * * * *